June 23, 1936. N. M. SMITH Plant Pat. 188
ORNAMENTAL CHERRY TREE
Filed July 2, 1935
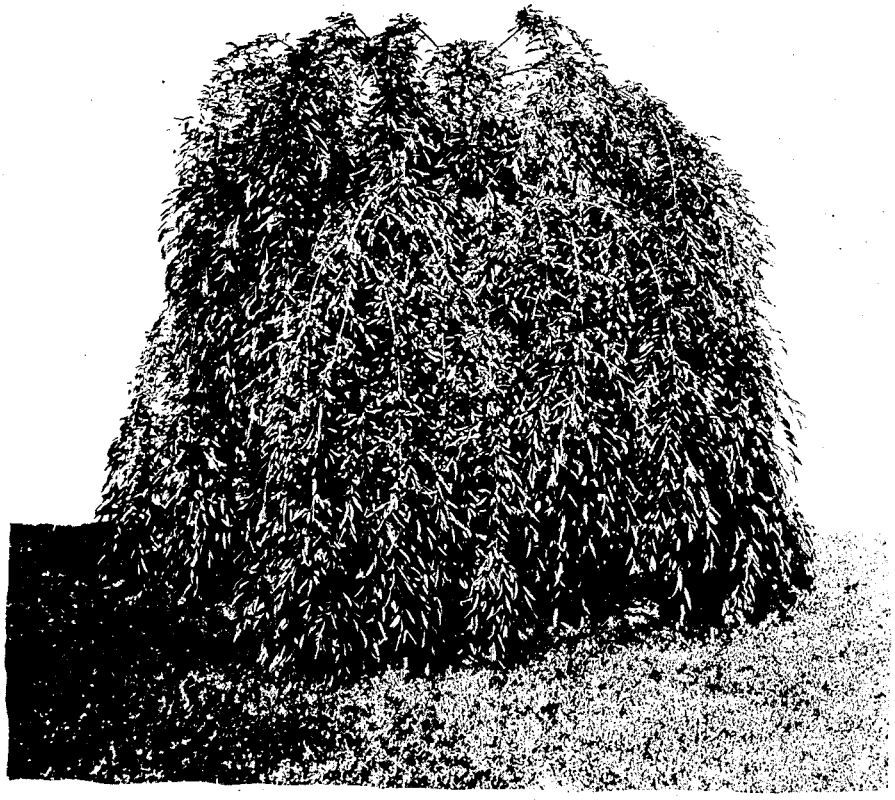
INVENTOR
NEVILLE MITCHELL SMITH
BY Malcolm F. Gannett
ATTORNEY Patented June 23, 1936

Plant Pat. 188

UNITED STATES PATENT OFFICE

188

ORNAMENTAL CHERRY TREE

Neville Mitchell Smith, York, Pa.

Application July 2, 1935, Serial No. 29,473

1 Claim. (Cl. 47—59)

This discovery relates to a new and distinct pendulous variety of ornamental cherry tree which includes the distinguishing characteristics hereinafter pointed out.

In the accompanying illustration the figure is a side elevation or perspective, showing the characteristic features of the new variety of plant.

The prominent distinctions and characteristics of the new variety of ornamental cherry tree are pointed out and become apparent from the following detailed description and annexed illustration, which is reproduced from a photograph taken of a tree located on my estate adjoining the city of York, on the 12th day of June, 1935; the tree being in full leaf. At the time the photograph was taken the tree was approximately seven years old, and had been blooming three years.

The particular tree illustrated was about ten feet tall and approximately the same length in breadth at the time the photograph was taken.

This tree was discovered by me and is believed to be the product of a mutant (a mutation), or an extreme variation from the usual types of ornamental cherry trees which have been developed in large quantities by nurserymen in this country, Japan, and other countries.

However, the present tree varies considerably from the usual ornamental Japanese type of cherry tree in that the limbs or branches extend upwardly at varying angles from the main trunk or body of the tree, and, as these limbs or branches become slenderer they curve downwardly forming many lateral branches which are long, extremely slender and extremely pendulous. As shown in the illustration, the drooping or depending branches of the tree carry a thick foliage of leaves which are joined to the long slender depending branches in a manner different from that found on the usual ornamental Japanese type of cherry tree.

The tree varies from the ordinary *Prunus subhirtella pendula,* in that the drooping branches are much longer, and the foliage more abundant, the branches carrying approximately one and one-third more leaves than the ordinary type of said species of weeping cherry trees. In autumn the foliage is a lovely bronze, turning to red and remains on the tree longer than other varieties. It also blooms a little earlier than some varieties.

The stem or trunk is unusually smooth and upright. The bark is much lighter in color and smoother than the bark of the ordinary type of weeping cherries; less inclined to knot, disease and gumming.

The principal difference or variaiton of the tree from the ordinary *Prunus subhirtella pendula,* is the habit of its growth. The branches are unusually uniform and less inclined to spread any distance from the trunk head than other varieties. The branches, in starting from the head, immediately proceed to take a drooping character and bend gracefully down to the ground, similar to a weeping willow (*Salix Babylonica*). Also the branches retain substantially the same thickness or caliber, almost from base to tip. Another noticeable feature of the tree is that the branches do not become twisted or knotty, but are very evenly placed, forming a beautiful, graceful, and attractive tree, both in growth, bloom and foliage.

The flowers borne by the tree are a lovely shade of light pink, almost white, and single, with from two to five petals, with a shallow notch at the apex. The flowers have a more prolific habit of blooming than the flowers of the ordinary type of *Prunus subhirtella pendula.*

The tree is a seedling from parents growing on my estate, was transplanted to its present location, and has been specially grown and tended solely by me.

Another characteristic of my tree is that the slender pendulous branches vary but slightly in their diameter along their entire length, many of them measuring from one-eighth to three-eighths of an inch in diameter where joining on to the trunk or larger branches and graduating down to their tips to a length of from four to twelve feet, thereby showing little or no difference in their diameters along their entire length.

The reproduction or propagation of this plant has been by asexual methods and has been propagated by me. The first tree of this type which I discovered was sprouting beneath a grafted ornamental cherry tree which I purchased about the year 1911. There are several new trees of this variety now growing on the grounds of my estate.

The fruit averages about one-quarter of an inch in diameter and consists of a comparatively large seed, surrounded by a thin layer of pulp which is enclosed by a thick or tough skin. I have noted that some species of birds relish the fruit, but otherwise the fruit is inedible.

The foliage has been known to remain until Christmas time.

The parentage of the tree is unknown.

All descriptive features not herein set forth are to be considered as substantially the same as those usually within the pendulous forms of *Prunus subhirtella.*

Having described the discovery what I claim is:—

An ornamental cherry tree (*Prunus subhirtella pendula*) as herein shown and described, characterized by having extremely long, slender, pendulous branches, starting from the head and immediately drooping and bending gracefully down to the ground, resembling the branches of a weeping willow (*Salix Babylonica*); having a stem or trunk unusually smooth and upright; the bark of the tree being lighter in color and smoother than the ordinary type of weeping cherries and less inclined to knot, disease and gum; and the branches carrying approximately one and one-third and more leaves than the ordinary type of *Prunus subhirtella pendula,* the color of the foliage becoming a lovely shade of bronze in the autumn which turns to red and remains on the tree longer than other varieties.

NEVILLE MITCHELL SMITH.